United States Patent [19]

Garland

[11] Patent Number: 5,065,894

[45] Date of Patent: Nov. 19, 1991

[54] DISPENSER FOR BANDAGES

[76] Inventor: Patricia A. Garland, 1618 Milton St., Tallahassee, Fla. 32303

[21] Appl. No.: 495,598

[22] Filed: Mar. 19, 1990

[51] Int. Cl.⁵ .............................................. B65H 5/28
[52] U.S. Cl. ..................................... 221/25; 221/72; 221/71
[58] Field of Search ............................ 221/25, 69–73, 221/89, 191, 194, 195, 197; 226/127, 134, 148, 152, 156, 157; 242/55.2

[56] References Cited

U.S. PATENT DOCUMENTS

| | | | |
|---|---|---|---|
| 53,199 | 3/1866 | Tonliff | 221/71 |
| 1,925,502 | 9/1933 | Schaeffer | 221/72 |
| 2,465,876 | 3/1949 | Hornung | 221/25 X |
| 3,653,539 | 4/1972 | Stageberg | 221/69 X |

Primary Examiner—David H. Bollinger
Attorney, Agent, or Firm—Arthur G. Yeager

[57] ABSTRACT

A dispenser for delivering an uncovered first aid bandage into a readily accessible outlet chute from a strip of bandage packages where each bandage is covered by a layer of paper on each side thereof prior to being dispensed. The dispenser has a spool for holding a supply roll of bandage packages, and two opposed press rollers receive and advance the strip therebetween. Two stripping rollers remove a cover strip of paper from each side of the package and deliver the strips to waste disposal and free the bandage. A ratchet on one of the press rollers is driven by a manually operated lever to rotate that roller, and a motion transmitting driving connection causes both press rollers to be turned equally in opposite directions.

20 Claims, 4 Drawing Sheets

DISPENSER FOR BANDAGES

BACKGROUND OF THE INVENTION

Packaged sterile bandages with adhesive tape included (popularly known as "Bandaids") are used in such volume that long strip packages of a plurality of such bandages are made and sold so the user can tear off one packaged bandage at a time when needed. Each separate package must, of course, be opened to strip away a layer of paper or foil on each side to free the sterile bandage for use. Normally, that use requires that a cover strip on each tape be removed as the bandage is applied to the wound. This preserves the sterile condition until applied. There has been a need for a device to dispense from a large supply strip one bandage at a time with the outer protective paper cover removed.

It is an object of this invention to provide a dispenser of individual bandages with adhesive tape applicators ready for use. It is another object of this invention to supply a dispenser of individual bandages from an elongated supply strip of such bandages. Still other objects will appear from the more detailed description which follows.

BRIEF SUMMARY OF THE INVENTION

This invention relates to a dispenser for individual adhesive tape bandages from an elongated strip package of said adhesive tape bandages including two outside strips of paper sandwiching therebetween a plurality of spaced adhesive tape bandages; said dispenser including a supply spool to hold a roll of said bandages in an elongated strip package, two press rollers biased toward each other and adapted to receive said strip therebetween two paper stripping rollers spring biased, respectively, against said press rolls and each adapted to receive separate ones of said outside strips of paper and direct them to waste disposal; a manually operated ratchet means attached to one of said press rollers to cause it to rotate and advance said strip passing between said rolls; and means to transfer the rotation of said one press roller into an equal and opposite rotation of the other said press roller.

In specific and preferred embodiments of the invention each stripping roller is spring biased to press against one of said press rollers and be driven in rotation by that press roller; one press roller contains a ratchet wheel which is turned by the movement of a manually operated lever with a ratchet pawl attached; and the press rollers and the stripping rollers are each covered with a rubber layer.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The invention is best understood by reference to the attached drawings.

Figure 1:
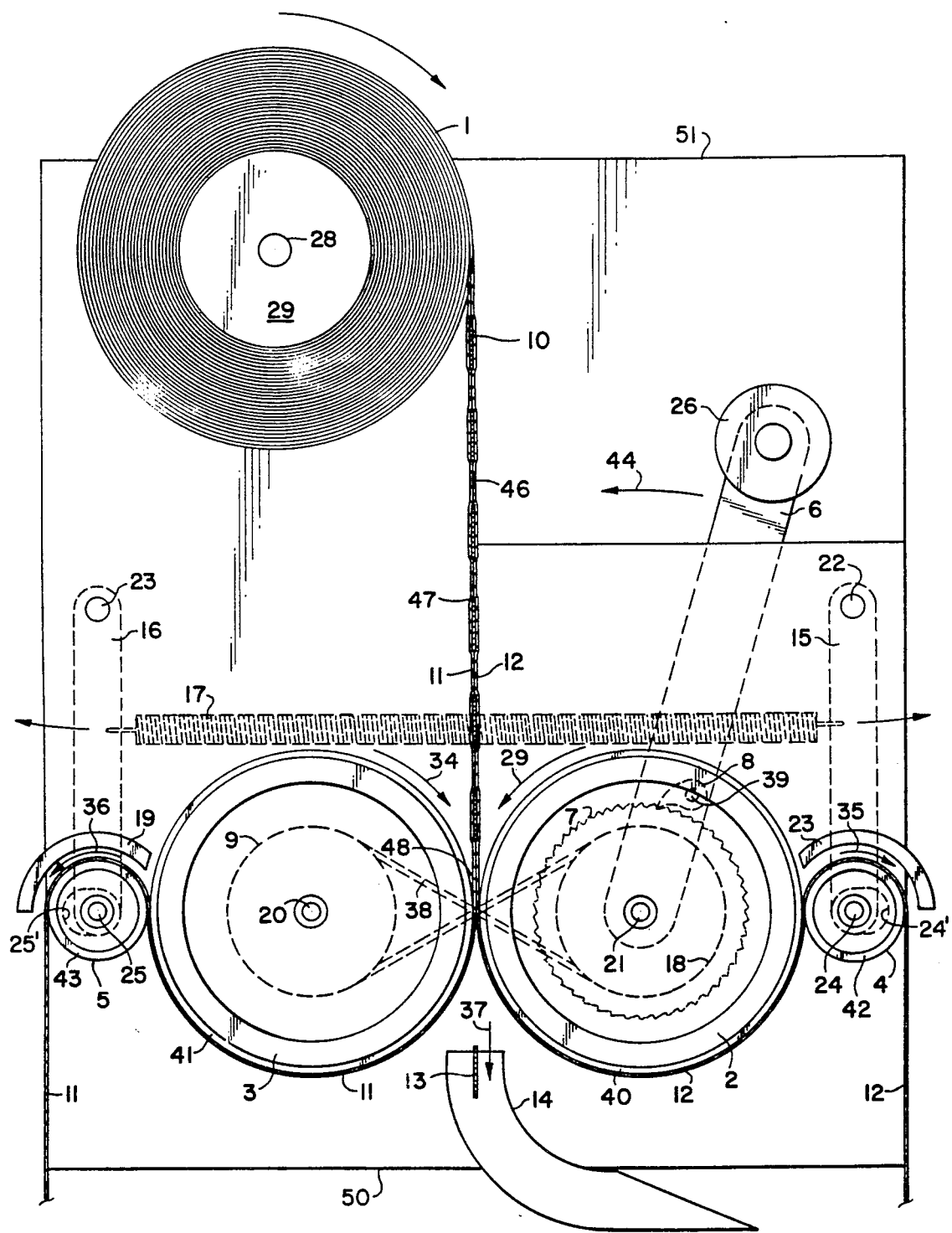
FIG. 1 is a front elevational view of the first embodiment of the dispenser of this invention.
Figure 2:
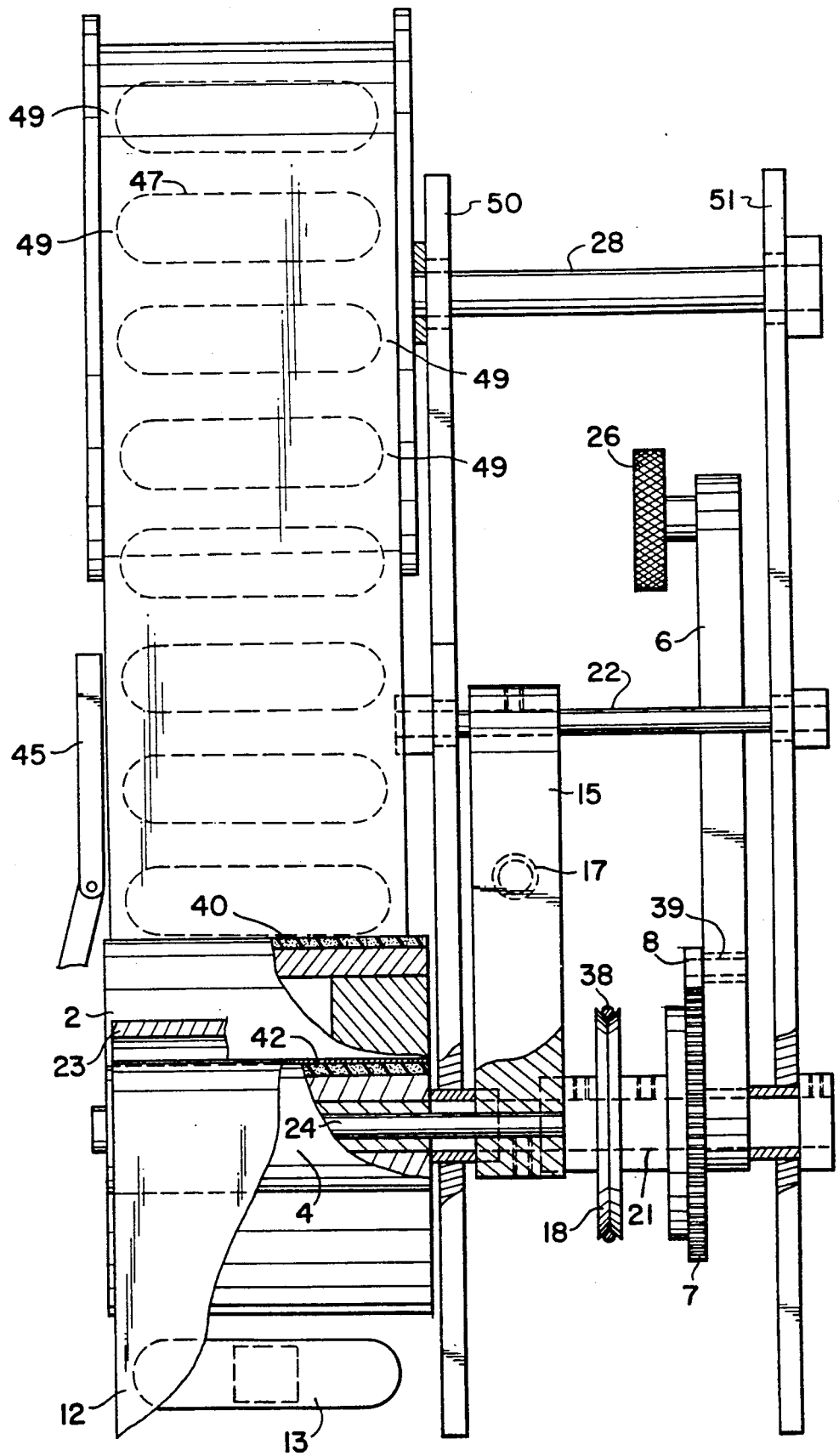
FIG. 2 is a partial side elevational view of the dispenser of FIG. 1 with parts in cross-section for clarity of illustration.

One embodiment is shown in FIGS. 1 and 2. A large roll 1 of a strip package containing a plurality of spaced adhesive tape bandage units 10, which may be separated by spaced and adhesively connected portions 46 with portions 49 similarly closing the ends around each bandage 47, is mounted on a spool 29 which is freely rotatable around shaft 28, mounted to a pair of spaced frame members 50 and 51. There may be a brake means (not shown) or merely a tight fit around shaft 28 to prevent spool 29 and roll 1 from unrolling too freely, and yet to be rotated as strip 47 moves from roll 1 to the nip 48 between rollers 2 and 3. Strip 47 does not require that there be a line of perforations through portions 46 between adjacent bandages 47 and it is preferable not to have such perforations.

Strip 47 advances toward press rollers 2 and 3 (downward in FIG. 1) to nip 48 between rollers 2 and 3. Rollers 2 and 3 engage strip 47 between them and move strip 47 downwardly (or forward) as rollers 2 and 3 rotate in the direction of arrows 29 and 34, around shafts 21 and 20, respectively. Rollers 2 and 3 may be movable so as to adjust the space between them at nip 48 or they may be immovable and merely positioned so as to provide a frictional grip on both sides of strip 47 where there are layers 11 and 12 of material, such as paper or foil. Preferably, each roller 2 and 3 is covered with a layer 40 and 41 of rubber or similar resilient frictional material to enhance the friction between the rollers 2 and 3 and strip 47.

One of press rollers 2 and 3 (2 in this embodiment) includes a driving means for causing it to be rotated and thereby to advance strip 47. In this embodiment roller 2 has a ratchet wheel 7 rigidly attached thereto which rotates with the rotating roller 2. A lever 6 with a knob or handle 26 is pivoted around shaft 21 which is the shaft on which roller 2 is mounted. Pawl 8, pivots around pin 39 mounted on lever 6 and catches in the teeth of ratchet wheel 7 as lever 6 is moved in the direction of arrow 44. Lever 6 may be spring biased in a direction opposite to arrow 44. One or more stops (not shown) may be positioned so that one stroke of lever 6 is sufficient to cause strip 47 to move forward sufficiently to dispense one bandage 10 and only one bandage, as illustrated by bandage 13. The lever 6 moves a predetermined distance corresponding to the rotative movement of the press rollers 2 and 3 to expose and release one bandage 13 from the strip 47, the rotative movement being substantially equal to a width of the bandage and a spacing between adjacent bandages. This rotative movement will permit both sides of the next bandage to be dispensed to remain sterile with all of the portions 46 and portions 49 remaining sealed, i.e., only about the upper one-half of the lowermost portion 46 remains sealed upon dropping of bandage 13 from between rollers 2 and 3.

In order to coordinate the movement of rollers 2 and 3 pulleys 18 and 9 are attached, respectively, and fitted with belt 38, which can be crossed in the middle as shown so as to make a counterclockwise movement of press roller 2 causing a similar clockwise movement of press roller 3.

Paper cover strips 11 and 12 are passed around the outside of press rollers 3 and 2 and onto stripping rollers 5 and 4, respectively. Rollers 5 and 4 are pressed against the outside of press rollers 3 and 2 with sufficient force to be rotated by frictional contact as each of press rollers 3 and 2 are rotated. The pressure on press rollers 3 and 2 is supplied by tension spring 17 which inter-connects levers 16 and 15. Thus the manual force applied to lever 6 causes press rollers 2 and 3 and stripping rollers 4 and 5 to rotate. Paper strips 11 and 12 are discharged from rollers 5 and 4 to a waste bin (not shown) but positioned generally below the chute 14. Stripping rollers 4 and 5 are respectively mounted on pivotable levers 15 and 16, pivoting around shafts 22, 23 mounted between frame members 50 and 51 with rollers 4 and 5 rotating around shafts 24 and 25, respectively, in the direction of arrows 35 and 36. Slots 24' and 25' in frame member 50 permits movement of the shafts 24 and 25. If desired, fenders 23 and 19 may be positioned over rollers 4 and 5 to help guide paper strips 12 and 11 to the waste bin. Layer 42 and 43 of rubber or the like may cover rollers 4 and 5 so that paper cover strips 12 and 11 may be properly positioned.

As paper cover strips 11 and 12 are separated and stripped away over press rollers 2 and 3 to stripping rollers 4 and 5, individual unencapsulated bandages, as at 13, are dropped downward for application onto a patient. A dispensing chute 14 is positioned to catch bandage 13 and deliver it to the outlet for receipt by the nurse or doctor onto a patient.

Figure 3:
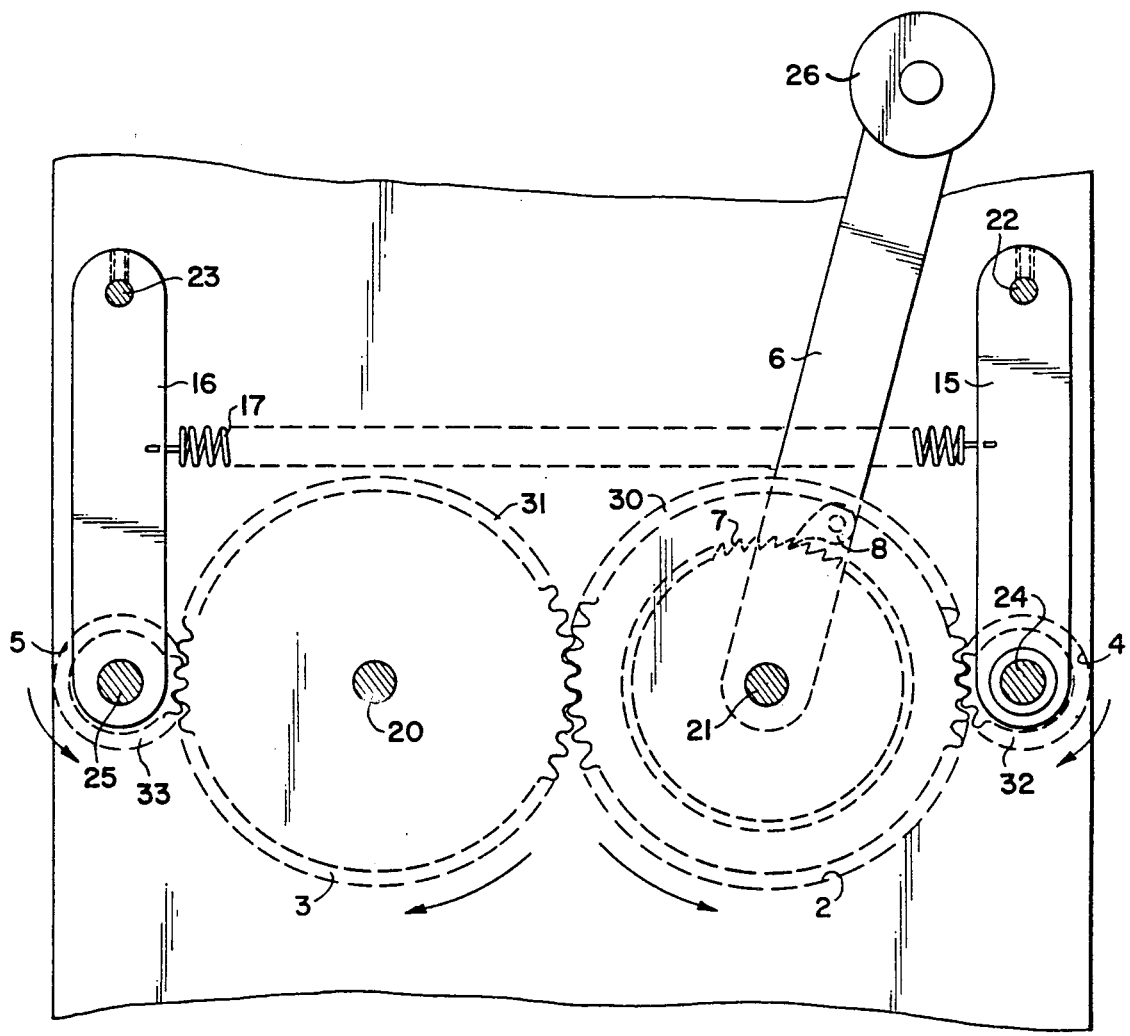
FIG. 3 is a partial front elevational view of a second embodiment of the dispenser of this invention.
Figure 4:
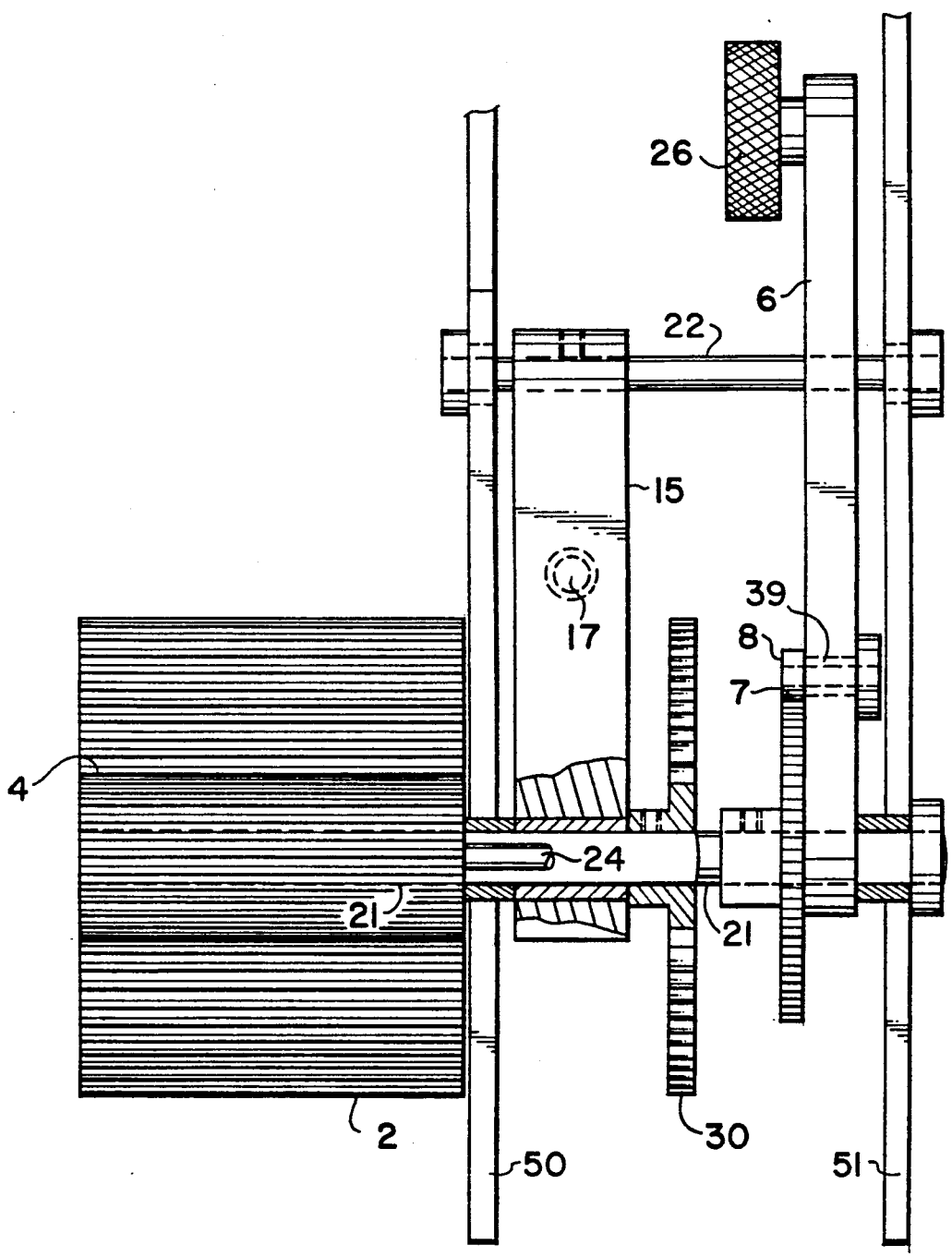
FIG. 4 is a partial side elevational view of the dispenser of FIG. 3 with parts in cross section for clarity of illustration.

A second, and preferred, embodiment is shown in FIGS. 3 and 4 wherein gear wheels 30 and 31 are on press rollers 2 and 3 rather than pulleys 18 and 9 and belt 38 of FIGS. 1 and 2 to provide for transmitting movement from press roller 2 to press roller 3. Similarly, gear wheels 32 and 33 are on stripping rollers 4 and 5 to transmit the movement in a positive manner rather than rely solely on the frictional contact between the belt 38 and pulleys 38 as in FIGS. 1 and 2. Other than such modifications, the operation and structure of this second embodiment is essentially the same as that described above with respect to FIGS. 1 and 2. In this preferred embodiment it is not necessary that rollers 2 and 3 bear against each other, but only that they be close enough to guide strips 47 through nip 48. The positive driving of gear wheels 32 and 33 will pull cover strips 12 and 13 away from bandage 13 and free it to drop into chute 14.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A dispenser for individual adhesive tape bandages from an elongated strip package of said adhesive tape bandages including two outside strips of paper sandwiching therebetween a plurality of spaced adhesive tape bandages; said dispenser including a supply spool to hold a roll of said bandages in an elongated strip package, two press rollers aligned and spaced apart so as to receive said strip therebetween, two paper stripping rollers biased respectively against said press rollers and each adapted to receive separate ones of said outside strips of paper and direct them to waste disposal; a manually operated ratchet means attached to one of said press rollers to cause it to rotate and advance said strip passing between said rolls; means to transfer the rotation of said one press roller into an equal and opposite rotation of the other said press roller; and an outlet located beneath said press rollers for receiving a freely falling said adhesive tape bandage released from said outside strips of paper upon manual operation of said ratchet means.

2. The dispenser of claim 1 wherein said spring biased stripping rollers are urged toward one another against opposite sides of said two press rollers to cause them to be pressed together.

3. The dispenser of claim 1 wherein said strip package includes a plurality of elongated adhesive tape bandage units spaced apart from each other and oriented so as to be positioned with their long axes perpendicular to the long axis of said strip.

4. The dispenser of claim 1 wherein said means to transfer the rotation of said one press roll to an equal and opposite rotation of the other roll includes a pulley on each said press roller and continuous belt drivingly connected said pulleys.

5. The dispenser of claim 1 wherein said means to transfer the rotation of said one press roll to an equal and opposite rotation of the other roll includes a gear train connecting said two press rollers.

6. The dispenser of claim 1 which additionally comprises spring means urging said stripping rollers against said press rollers.

7. The dispenser of claim 6 wherein each said stripping roller is mounted on a pivotable lever to which is attached said spring means.

8. The dispenser of claim 1 wherein said ratchet means includes a manually movable lever containing a pivotable pawl adapted to engage a ratchet wheel mounted on one said press roller.

9. The dispenser of claim 1 wherein each said press roller and each said stripping roller is covered with a resilient layer of rubber.

10. The dispenser of claim 1 wherein said ratchet means includes a ratchet wheel mounted on one said press roller and a manual lever and pawl engaged with said ratchet wheel to move said press rollers sufficiently to cause release of one said bandage from between said press rollers.

11. The dispenser of claim 1 wherein said driving means includes a manually movable lever carrying a pivotable pawl, a ratchet wheel mounted on one said press roller engaged with said pawl and adapted to be driven by said pawl upon movement of said lever.

12. The dispenser of claim 11 wherein said lever is movable a predetermined distance, said distance corresponding to rotative movement of said press rollers sufficiently to expose and release one said bandage from said strip, said bandages being elongated and positioned with their longitudinal axis parallel to rotative axes of said press rollers, said rotative movement being substantially equal to a width of said bandage and a spacing between adjacent bandages.

13. The dispense of claim 1 wherein each said press roller and each said stripping roller is covered with a resilient layer of friction enhancing material.

14. A dispenser for individual adhesive tape bandages from an elongated strip package of said adhesive tape bandages including two outside strips of material sandwiching therebetween a plurality of spaced adhesive tape bandages; said dispenser including a supply spool to receive a roll of said bandages in said elongated strip package, two roller for receiving and feeding therebetween a portion of said strip package, two paper stripping rollers biased respectively said outside strips of material and direct same to a waste disposal; driving means attached to one of said press rollers to cause it to rotate and advance said strip portion passing between said press rollers sufficiently to cause the release of one said bandage therefrom; an elongated outlet chute having an upper end portion located beneath said press rollers for receiving said one bandage and conveying same to a lower end portion of said chute disposed in an accessible position for ready removal of said one bandage; and means to transfer the rotation of said one press roller into an equal and opposite rotation of the other said press roller.

15. The dispenser of claim 14 wherein each said bandage is elongated and spaced apart from the next and oriented so as to be positioned with its longitudinal axis parallel to rotative axis of said press rollers.

16. The dispenser of claim 14 wherein said means to transfer the rotation includes a pulley on each said press roller and a continuous belt drivingly connecting said pulleys.

17. The dispense of claim 14 wherein said means to transfer the rotation includes a gear train connecting said two press rollers.

18. The dispenser of claim 14 wherein said spring biased stripping rollers are urged toward one another against opposite sides of said two press rollers to cause them to be pressed together and to rotate oppositely to respective said press rollers.

19. The dispenser of claim 18 which additionally comprises spring means urging said stripping rollers against said press rollers.

20. The dispenser of claim 19 wherein each said stripping roller is mounted on a pivotable lever to which is attached said spring means.

* * * * *